United States Patent [19]

Milligan

[11] Patent Number: 4,465,876

[45] Date of Patent: Aug. 14, 1984

[54] NITRATION OF AROMATICS WITH NITROGEN OXIDES IN TRIFLUOROACETIC ACID

[75] Inventor: Barton Milligan, Coplay, Pa.

[73] Assignee: Air Products and Chemicals, Inc., Allentown, Pa.

[21] Appl. No.: 464,240

[22] Filed: Feb. 7, 1983

[51] Int. Cl.³ .............................................. C07C 79/10
[52] U.S. Cl. .................... 568/940; 568/630; 568/937; 568/938; 568/939
[58] Field of Search .............. 568/630, 937, 938, 939, 568/940

[56] References Cited

U.S. PATENT DOCUMENTS 3,415,868 12/1968 Smetana et al. ................ 260/466
3,950,385 4/1976 Kablaoui ........................ 260/466
4,417,080 11/1983 Ross et al. ...................... 568/939

OTHER PUBLICATIONS

U. A. Spitzer and R. Stewart, J. Org. Chem., 1974, 39, 3936.
Richard O. C. Norman, et al., in J.C.S. Perkin 1, 1974, 369.
Sake Vemura, et al., in J.C.S. Perkin 1, 1978, 1077.

Primary Examiner—Leland A. Sebastian
Attorney, Agent, or Firm—Mark L. Rodgers; E. Eugene Innis; James C. Simmons

[57] ABSTRACT

In a process for nitrating aromatics using lower valent nitrating agents in trifluoroacetic acid, the product yield of nitroarenes can be significantly increased by maintaining an excess of nitrating agent over the stoichiometric amount during the reaction.

10 Claims, No Drawings

NITRATION OF AROMATICS WITH NITROGEN OXIDES IN TRIFLUOROACETIC ACID

TECHNICAL FIELD OF THE INVENTION

The present invention relates to an improved process for nitrating toluene, benzene and other aromatics with lower valent nitrogen oxides, or precursors thereof, in trifluoroacetic acid.

BACKGROUND OF THE INVENTION

Aromatic nitro compounds are broadly useful intermediates. They can be synthesized in a number of ways, but the most common method employs mixtures of nitric and sulfuric acids. In operating this method however, a spent sulfuric acid containing water is formed from the nitration process and it must be reclaimed if large scale nitration is to be at all economical. Since recovery of spent sulfuric acid is expensive, primarily due to energy costs associated with the removal of water, other methods of nitration are of continued interest.

One alternate method involves using a trifluoroacetic acid medium in place of sulfuric acid. Trifluoroacetic acid has a boiling point of 72° C. Because of this low boiling point, the acidic solvent for the nitration reaction can be recovered by distillation using exhaust steam as a source of heat.

An important consideration in choosing a particular medium for nitrating aromatics is the ability to carry out the nitration reaction using lower valent; N(III) and N(IV); nitrogen compounds. By using a nitrogen oxide, less $H_2O$ is produced during the nitration process allowing for easier separation of the reaction products. N(III) and N(IV) oxides are more readily available and less expensive than N(V) oxide.

U. A. Spitzer and R. Stewart, J. Org. Chem., 1974, 39, 3936 disclose nitrating aromatics in the presence of a trifluoroacetic acid medium. In one example benzene and sodium nitrate were reacted together in a 1:1 molar ratio at room temperature to form nitrobenzene in a 99.9% yield. In another example sodium nitrite was reacted with benzene in the same 1:1 molar concentration and at the same temperature as the nitrate example, however, nitrobenzene yield was only about 3%.

Richard O. C. Norman, et al. in J. C. S. Perkin I, 1974, 369 disclose nitrating aromatics with nitrogen dioxide in the presence of trifluoroacetic acid. In one series of runs nitrogen dioxide was bubbled through a solution of benzene in trifluoroacetic acid at temperatures from 0°-100° C. and with reaction times from 1-5 hours. Nitrobenzene yields ranged from about 2% to 54%. It was reported however, that adding urea to the system increased the nitrobenzene yield up to as much as 99%.

Sake Uemura, et al. in J. C. S. Perkin I, 1978, 1077 disclose nitrating aromatics using stoichiometric amounts of arenes and nitrating agents in the presence of trifluoroacetic acid at 25° C. When sodium nitrate was added to benzene, or a derivative thereof, the nitroarene yields were reported to be as high as 100%. Similarly, when sodium nitrite was used in the 3:1 stoichiometric ratio, instead of sodium nitrate, under the same reaction conditions, nitroarene yields were again reported to be as high as 100%. When the reaction was run under the conditions employed by Spitzer and Stewart; 1:1 molar ratio of arene to nitrating agent in 340 mmol of trifluoroacetic acid at 25° C.; nitroarene yield was reported at only 20%.

SUMMARY OF THE INVENTION

It has been found that, in reactions using lower valent nitrogen oxides to nitrate aromatic compounds in trifluoroacetic acid, the yield of nitroaromatic product improves as the ratio of nitrating agent to substrate increases over the stoichiometric requirement.

Specifically, in a process for forming a nitroaromatic hydrocarbon by reacting nitrogen dioxide, an aromatic compound and trifluoroacetic acid, the yield of said nitroaromatic hydrocarbon can be enhanced by maintaining a molar ratio of at least 2:1 of said nitrogen dioxide to said aromatic during said reaction.

Similarly, in a process for forming a nitroaromatic hydrocarbon by reacting a nitrite salt or nitrous acid, an aromatic compound and trifluoroacetic acid, the yield of said nitroaromatic hydrocarbon can be enhanced by maintaining a molar ratio of at least 5:1 of said nitrite salt or nitrous acid to said aromatic during said reaction.

DETAILED DESCRIPTION OF THE INVENTION

In the operation of the method of the invention an aromatic hydrocarbon is contacted in the presence of trifluoroacetic acid with an excess over the stoichiometric amount of nitrogen dioxide, nitrous acid or a nitrite salt.

The trifluoroacetic acid medium should be present in a conventional amount, i.e., a concentration sufficient to allow nitration to occur. Any excess over this minimum amount is not necessary and does not appear to have any effect on the reaction. The concentrations reported in the examples based upon the aromatic hydrocarbons are representative and not critical and therefore are not meant to be limiting.

Nitration can take place at a wide range of temperatures and pressures as noted in the art. However, it is generally preferred that the temperature range be maintained between 20° C. and 30° C. and the pressure at about 1 atmosphere.

The aromatic hydrocarbons nitrated by the technique described are generally mononuclear and usually benzene or toluene or any common derivative thereof; e.g. xylene, anisole, ethylbenzene, isopropylbenzene, butylbenzene, cymene and halogenated benzenes.

The nitrating agent used in effecting nitration of the aromatic compound is nitrogen dioxide. Nitrogen dioxide can exist in that form or be generated from precursors thereof; e.g. from N(III) and N(IV) nitrogen oxides. Examples of nitrogen oxides capable of generating $NO_2$ for effective nitration are $N_2O_3$ and $N_2O_4$; and for purposes of this invention the precursors are encompassed by the term nitrogen dioxide. $N_2O_3$ is unstable and generally does not exist in that form. It will decompose to a mixture of nitrogen dioxide and nitrogen monoxide or form nitrous acid on contact with water.

Nitrogen dioxide may also be generated from nitrite salts, the salt being attacked by the acid to generate nitrous acid which decomposes to nitrogen dioxide and other products. Nitrite salts used in effecting nitration of the aromatics are known and typically comprise alkali metal nitrite salts; e.g. sodium and postassium nitrite.

It was found that in order to produce a good nitroarene yield or selectivity with little oxidative by-product formation when using $NO_2$ as the nitrating agent, a molar ratio of at least 2:1 and preferably about 7:1 or greater of NO₂ to aromatic should be maintained during the reaction. This is considerably greater than the stoichiometric ratio of 3:2. When one uses a precursor nitrogen oxide to generate nitrogen dioxide, the required concentration of nitrogen dioxide in the reaction medium remains the same. However, for purposes of calculating the number of moles of precursor for the maintenance of a molar ratio of nitrogen dioxide of at least 2:1 during the reaction, the stoichiometric chemical reactions are utilized. The moles of precursor are then adjusted so that the net result is the generation of a reaction mixture in which the molar ratio of nitrogen dioxide is at least 2:1.

For NaNO₂, a molar ratio of at least about 5:1 and preferably about 8:1 or greater of NaNO₂ to aromatic is required. This is also much greater than the stoichiometric ratio of 3:1 for this reaction. Molar ratios lower than these produce poor yields of nitroarenes and large amounts of oxidative by-products such as phenols, cresols and derivatives thereof.

When the reaction is carried out according to the above conditions only mononitration is observed. The distribution of isomers obtained from the nitration of toluene is significantly, but not radically different from that found when N(V) nitrating agents are used in a sulfuric acid medium. The distribution ratio for O/P is about 1.3 (VS 1.8) and about 1.5% of m-isomer is formed (VS 4-5%).

Although not intended to be bound by theory, it is believed that the need for a large excess of nitrating agent over the stoichiometric amount, in order to obtain high selectivity, can be explained by the following proposed mechanism.

N(IV) reactants, either N₂O₄ or NO₂ disassociate to form NO₃⁻ and NO+ which forms the nitrosonium-arene complex (A). N(III) reactants react with the trifluoroacetic acid to form HNO₂ which in turn forms N₂O₃ and H₂O. The N₂O₃ disassociates to form NO₂⁻ and NO+ which forms the nitrosonium-arene complex (A).

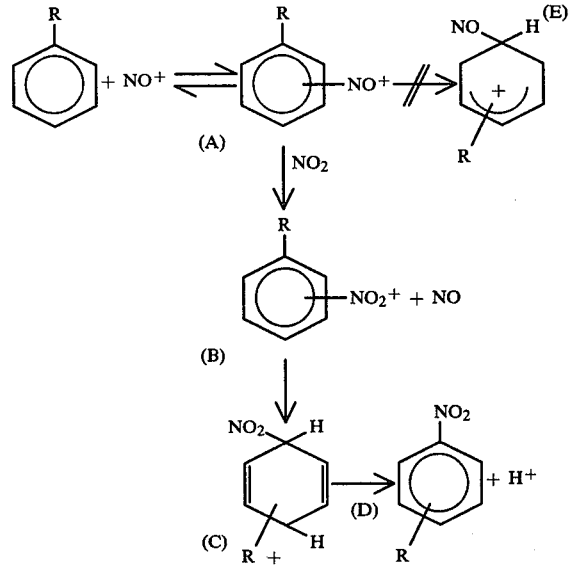

Oxidation of the nitrosonium-arene complex (A) by nitrogen dioxide yields the nitronium complex (B) which immediately collapses to nitro product (D) through cyclohexadienyl intermediate (C). The rapid oxidation by NO₂ is the key step in obtaining high selectivity. Competing with this process is oxidative reaction or reactions upon the free hydrocarbon resulting in unwanted oxidative by-products (E). When the concentration of aromatic compound to nitrogen dioxide approaches stoichiometric quantities, the aromatic compound can complex with the nitrosonium ion and become unavailable to the competing oxidative route. This explains the shift from oxidized to nitrated products as the ratio of reagent to substrate is increased. When nitrite salts are used as the precursor for nitrogen dioxide higher concentrations of salt are required to achieve high selectivity. This phenomenon is caused by the rate limiting decomposition step of the nitrite salt. In order to maintain high levels of nitrogen dioxide in the reaction medium, higher levels of nitrite salt must be used as compared to when nitrogen dioxide is used.

The following examples are illustrative of the above-described invention and are not meant to be limiting.

EXAMPLES

A predetermined amount of sodium nitrite or nitrogen dioxide was dissolved in trifluoroacetic acid at room temperature in a tubular vessel attached to a vacuum system by customary vacuum techniques thereby avoiding the presence of any oxygen or air. NaNO₃ was also used as a control. A small amount of nitric oxide was given off as a result of this mixing. A measured amount of benzene, toluene, or another reactive aromatic was then added to this solution by vacuum line transfer. This reaction mixture was worked up by quenching in water, extraction with methylene chloride, reextraction with water to remove TFA, extraction with 1% sodium carbonate to remove acidic by-products and drying with calcium sulfate. The sodium carbonate extracts were acidified to pH 1 with sulfuric acid and extracted 3-4 times with ether. The dried ether solutions were examined by thin layer and/or liquid chromatography. Nitroarene products were analyzed by gas chromotography on a 25 m dimethyl silicone capillary column using nitrobenzene as internal standard for nitrotoluene and p-nitrotoluene as internal standard for nitrobenzene. Response factors were measured from mixtures approximating the compositions of those analyzed. The internal standard was generally added to the initial reaction mixture. A Finigan OWA model gas chromatograph/mass spec. was used by the Air Products Corporate Research Service Department.

The results of these runs, along with two runs reported by Uemura, et al, are reproduced in Table 1.

TABLE I

RESULTS
NITRATION OF BENZENE AND TOLUENE BY N(III), N(IV) AND N(V) IN TFA

| Entry | Substrate (m mole) | Reagent | $\frac{\text{m mole R}}{\text{m mole S}}$ | Vol-TFA mL | Yield ArNO$_2$ Based on Arene | Isomer o/p | Ratios % m | Phenolic Products |
|---|---|---|---|---|---|---|---|---|
| Entry | | | | | | | | |
| 1 | Toluene (10.9) | NaNO$_3$ | 1.08 | 15 | 97% | 1.38 | 1.2 | ND[a] |
| 2 | Toluene (2.2) | NaNO$_2$ | 2.5 | 15 | 17% | 1.33 | | p-HOPhCO$_2$[b] 7.3% DNOC[b] 5.2T DNPC[b] |
| 3 | Toluene (1.10) | NaNO$_2$ | 6.3 | 15 | 47.6% | 1.37 | | 45% DNC |
| 4 | Toluene (9.99) | NaNO$_2$ | 6.7 | 50 | 52.7% | 0.99 | 4.3 | 3.0% DNOC 1.6% DNPC |
| 5 | Toluene (1.24) | NaNO$_2$ | 7.8 | 15 | 91.5% | 1.32 | 1.3 | ND[a] |
| 6 | Benzene (2.3) | NaNO$_2$ | 2.6 | 15 | 51% | — | — | ND[a] |
| 7 | Benzene (1.05) | NaNO$_2$ | 4.8 | 15 | 77.6% | | | .9% DNP[c] 10.8% PA[c] |
| 8 | Toluene (11.0) | NO$_2$ | 1.7 | 15 | 82%[d] | 1.32 | 1.5 | ND[a] |
| 9 | Toluene (2.15) | NO$_2$ | 6.3 | 10 | 95.4% | 1.30 | 1.1 | ND[a] |
| 10 | Toluene | NO$_2$ | 7.7 | 15 | 100%[d] | 1.38 | 1.1 | ND[a] |
| Uemura | | | | | | | | |
| 11 | Benzene (2.0) | NaNO$_2$ | 3.0 | 15.4 | 97%[e] | — | — | |
| 12 | Toluene (2.0) | NaNO$_2$ | 3.0 | 15.4 | 100%[e] | 1.35 | 1.0 | |

[a]ND = not determined
[b]DNOC = 2,4-dinitro-o-cresol DNPC = 2,6-dinitro-p-cresol
[c]DNP = 2,4-dinitrophenol, PA = picric acid
[d]Product analyzed without aqueous workup
[e]Not know what % yield is based on The Control run, run 1, produced a 97% nitroarene yield when NaNO$_3$ was reacted with toluene in trifluoroacetic acid. This reaction however results in larger amounts of water being formed and consequently results in a more difficult and costly separation process than when lower valent nitrogen is employed.

Runs 2 through 5 show the results of reactions using various amounts of NaNO$_2$ reagent with toluene as the substrate. The stoichiometry of this reaction is such that 3 mmols of NaNO$_2$ are required to nitrate 1 mmol of toluene. In run 2, 2.5 mmoles of NaNO$_2$ per mole of toluene were reacted. The nitroarene yield based upon the amount of toluene used was only 17%.

Uemura, et al. using the stoichiometric 3:1 molar ratio of NaNO$_2$ to toluene under similar conditions reported nitroarene yields of up to 100%. See entry 12, Table I.

In run 3, 6.3 mmoles; more than twice the stoichiometric amount; of NaNO$_2$ per mmole of toluene were reacted. The nitroarene yield was 47.6%. In run 4 the level of nitrating agent was increased to provide an R/S ratio of 6.7/1. Selectivity increased as compared to runs 2 and 3. However, it was not until run 5, when the molar ratio of NaNO$_2$ to toluene was increased to 7.8 that a good yield, 91.5%, of nitroarene product was produced. The good yields obtained by Uemura using stoichiometric amounts of substrate and nitrating agent could not be duplicated and, as can be seen from runs 2–5, more than twice the stoichiometric amount of nitrating agent had to be used before our results approached those reported by Uemura.

Similar results were obtained when benzene was used as a substrate with NaNO$_2$ reagent as can be seen from runs 6 and 7. When a 2.6 molar ratio of NaNO$_2$ to benzene was used a 51% product yield was obtained. When the molar ratio was increased to 4.8, considerably above the 3.0 stoichiometric ratio, product yield was still only 77.6%. These results are far less than the 97% yield reported by Uemura using stoichiometric amounts of NaNO$_2$ and benzene under similar reaction conditions. See entry 11, Table I.

It is not understood why these results differ from those reported by Uemura. One possible explanation could be the type of analytical techniques used to determine the reaction products. What is known from the data, however, is that when nitrating aromatic hydrocarbons with lower valent nitrogen oxides under the conditions described above, good nitroarene product yield is not obtained unless an excess of nitrating agent is maintained during the reaction. This result is surprising since generally it is not expected that increasing the concentration of one reactant over what is required by the stoichiometry of the particular reaction would increase the amount of product formed.

Additional reactions were run using NO$_2$ as the nitrating agent and toluene as the substrate. The results of these reactions are reported in table 1, runs 8–10. The stoichiometric ratio for this reaction is 1.5 mmole NO$_2$ per mmole of toluene. Although nitroarene yields were larger when NO$_2$ was used in place of NaNO$_2$, it can still be seen that as the concentration of nitrating reagent is maintained from close to the stoichiometric amount (run 8) to amounts far exceeding the stoichiometric requirement (runs 9 and 10), nitroarene product yield also increases. These results are much greater than those obtained by Norman by bubbling an excess of NO$_2$ through the reaction mixture without the addition of urea. This illustrates why it is important that an excess of nitrating agent be maintained in the reaction mixture for the duration of the reaction.

Having thus described the present invention, what is now deemed appropriate for Letters Patent is set out in the following appended claims.

What is claimed is:

1. In a process for forming a nitroaromatic hydrocarbon by reacting nitrogen dioxide, an aromatic compound and trifluoroacetic acid in a vessel under conditions effective for forming said nitroaromatic, the improvement for enhancing the yield of said nitroaromatic product based upon said aromatic compound which comprises:

maintaining a molar ratio of at least 2:1 of said nitrogen dioxide to said aromatic during said reaction.

2. A process according to claim 1 wherein the aromatic compound is benzene.

3. A process according to claim 1 wherein the aromatic compound is toluene.

4. A process according to claim 1 wherein the reaction is carried out between 20°–30° C.

5. A process according to claim 1 wherein the said molar ratio is between about 2:1 to 7:1.

6. In a process for forming a nitroaromatic hydrocarbon by reacting a nitrite salt or nitrous acid, an aromatic compound and trifluoroacetic acid in a vessel under conditions effective for forming said nitroaromatic, the improvement for enhancing the yield of said nitroaromatic product based upon said aromatic compound which comprises:

maintaining a molar ratio of at least 5:1 of said nitrite salt or nitrous acid to said aromatic during said reaction.

7. A process according to claim 6 wherein the aromatic compound is benzene.

8. A process according to claim 6 wherein the aromatic compound is toluene.

9. A process according to claim 6 wherein the reaction is carried out between 20°–30° C.

10. A process according to claim 6 wherein the said molar ratio is between about 5:1 to 8:1.

* * * * *